United States Patent
Pearson et al.

(10) Patent No.: US 7,650,262 B2
(45) Date of Patent: Jan. 19, 2010

(54) METHOD, SYSTEM, AND SOFTWARE FOR ANALYZING PHARMACOVIGILANCE DATA

(75) Inventors: Ronald Pearson, Harrisburg, PA (US); Robert J. Kingan, Peachtree City, GA (US); Alan M. Hochberg, Harrisburg, PA (US)

(73) Assignee: Prosanos Corp., La Jolla, CA (US)

(*) Notice: Subject to any disclaimer, the term of this patent is extended or adjusted under 35 U.S.C. 154(b) by 805 days.

(21) Appl. No.: 11/257,395

(22) Filed: Oct. 25, 2005

(65) Prior Publication Data

US 2006/0111847 A1    May 25, 2006

Related U.S. Application Data

(60) Provisional application No. 60/621,078, filed on Oct. 25, 2004, provisional application No. 60/645,609, filed on Jan. 24, 2005.

(51) Int. Cl.
*G06F 17/10* (2006.01)
(52) U.S. Cl. ............... 703/2; 700/90; 702/19; 703/11
(58) Field of Classification Search ............ None
See application file for complete search history.

(56) References Cited

U.S. PATENT DOCUMENTS

2002/0183965 A1  12/2002  Gogolak
2003/0046110 A1  3/2003  Gogolak
2004/0117126 A1  6/2004  Fetterman et al.

OTHER PUBLICATIONS

International Search Report PCT/US05/38326 dated Jul. 7, 2008.
Manfred Hauben et al., "Potential Use of Data-Mining Algorithms for the Detection of 'Surprise' Adverse Drug Reactions", Drug Safety 2007: 30(2) 143-155.
June Almenoff et al., "Perspective on the Use of Data Mining in Pharmacovigilance", Drug Safety 2005: 28(11) 981-1007.
Emma Heeley et al., "Automated Signal Generating in Prescription-Event Monitoring", 2000, 25 (6) 423-432., Drug Safety.
William Dumouchel, "Bayesian Data Mining in Large Frequency Tables With an Application to the FDA Spntaneous Reporting System", AT&T Labs—Research, Florham Park, NJ, Apr. 1999, pp. 1-31.
A. Lawrence Gould, "Practical pharmacovigilance analysis strategies", Pharmacoepidemiology & Drug Safety, 2003: 12: 559-574.

(Continued)

*Primary Examiner*—Carolyn L. Smith
(74) *Attorney, Agent, or Firm*—Stephen A. Bent; Foley & Lardner LLP

(57) ABSTRACT

A computer-implemented method of analyzing a dataset of pharmacovigilance data, includes determining a sample size-independent measure of association between two conditions of interest in the dataset of pharmacovigilance data; using a hypergeometric distribution to determine a measure of statistical unexpectedness between the conditions of interest in said dataset, wherein the distribution is based on an urn model under a hypothesis that the conditions are statistically independent; and displaying the measure of association with the measure of the statistical unexpectedness to identify a significant association between conditions of interest.

31 Claims, 9 Drawing Sheets

OTHER PUBLICATIONS

Ethan D. Montag et al., "The Use of Color in Multidimensional Graphical Information Display", The Seventh IS&T/SID Color Imaging Conference; color Science, Systems & Applications, Scottsdale, AZ, 1999.

"Guidance for Industry Good Pharmacovigilance Practices & Pharmacoepidemiologic Assessment", U.S. Department of Health & Human Services, Food & Drug Administration, Center for Drug Evaluation & Research (CDER) Center for Biologics Evaluation & Research (CBER), Mar. 2005, pp. 1-20.

A. Bate et al., "A Bayesian neural network method for adverse drug reaction signal generation", Eur J Chem Pharmacol (1998), 54: 315-321.

Elliot G. Brown et al., "The Medical Dictionary for Regulatory Activities", Drug Safety, Feb. 1999, 20(2), 109-117.

William Dumouchel, "Bayesian Data Mining in Large Frequency Tables, With an Application to the FDA Spontaneous Reporting System", The American Statistician, Aug. 1999, vol. 53, No. 3, pp. 177-190.

William Dumouchel et al., "Empirical Bayes Screening for Multi-Item Associations", Proceedings of the Seventh ACM SIGKDD International Conference on Knowledge Discover & Data Mining, Aug. 2001, pp. 67-76.

S.J.W. Evans et al., "Use of proportional reporting ratios (PRRs) for signal generation from spontaneous adverse drug reaction reports", Pharmacoepidemiology & Drug Safety 2001: 10; 483-486.

A.D. Gordon, "Classification $2^{nd}$ Edition", Chapman & Hall/CRC, 1999, 3 pages.

A. Lawrence Gould, "Practical pharmacovigilance analysis strategies", Pharmacoepidemiology & Drug Safety 2003; 12: 559-574.

Jan Groetzner MD et al., "Airway Anastomosis Complications in De Novo Lung Transplantation With Sirolimus-Based Immunosuppression", The Journal of Heart & Lung Transplantation, vol. 23, No. 5, pp. 632-638, 2004.

Norman L. Johnson et al., "Chapter 6 Hypergeometric Distributions", Univariate Discrete Distributions, Second Edition, 1992, pp. 237-253.

Paul W. Mielke, Jr. et al., "7.3 Contingency Table Coomparisons Under the Null Hypothesis", Permutation Methods A Distance Function Approach, 2001, pp. 273-274.

Ana Szarfman et al., "Use of Screening Algorithms & Computer Systems to Efficiently Signal Higher-Than-Expected Combinations of Drugs & Events in the US FDA's Spontaneous Reports Database", Drug Safety, 2002: 25(6): 381-392.

Peter H. Westfall et al., "Resampling-Based Multiple Testing Examples & Methods for p-Value Adjustment", A Wiley Interscience Publication, John Wiley & Sons Inc., 1993, 4 pages.

METHOD, SYSTEM, AND SOFTWARE FOR ANALYZING PHARMACOVIGILANCE DATA

CROSS-REFERENCE TO RELATED APPLICATIONS

This application claims the benefit of priority under 35 U.S.C. §119(e) to U.S. provisional application No. 60/621,078 filed on Oct. 25, 2004, and U.S. provisional application No. 60/645,609 filed on Jan. 24, 2005, the disclosures of which are incorporated herein in their entireties.

BACKGROUND OF THE INVENTION

The present invention relates generally to the field of analyzing data for biological or medical tracking or monitoring purposes. More particularly, the present invention relates to analyzing data related to the safety of drugs, vaccines, medical devices, surgical procedures, and other therapeutic interventions for the treatment of disease in humans, animals, or agricultural plants.

Developers of pharmaceutical products, vaccines, medical products and the like are greatly concerned with the potential risk of harm to patients incidental to the use of these therapeutic interventions to treat disease. Agencies which regulate the sale and use of these products generally mandate a certain level of pharmacovigilance activity to measure and report adverse effects associated with the use of these products, in a way that attempts to ascertain whether or not a causal relationship exists between the use of the product and the adverse effect.

The evaluation of drug safety generally begins with in vitro toxicology studies in cultured cells and animals, and then proceeds to randomized, controlled clinical trials. In the present application, references to "drugs" may be understood to apply to vaccines, medical products, and the like as well. In a randomized, controlled clinical trial, a group of patients is divided into two groups. One half of the patients receive the drug under study, and the remainder receives a different "control" treatment, sometimes a placebo. More complex designs are possible as well, and often the assignment is done in a blind fashion so that neither the patient nor the investigator knows which patient has received which treatment until the conclusion of the study. In addition to comparing the efficacy of the drug under study versus the control, the relative safety of the two treatments is compared. This is done by compiling a table of all adverse events which occur. Adverse events are listed by a standardized code, such as the Medical Dictionary for Regulatory Activities (MedDRA) [Brown, 1999]. It should be noted that the complete citation for any referenced publication in provided at the end of this application in a separate section. For each adverse event code, the table includes the number of patients in the drug arm of the study who encountered that adverse event, and the number in the control arm of the study who encountered it as well. The adverse event table generally also includes percentages of the total population of each arm who experienced each type of adverse event. From this table, it is possible to calculate a relative risk for each event type associated with the drug as compared to the control.

Clinical trials must be conducted before a drug is marketed. Regulatory agencies such as the US Food and Drug Administration (FDA) decide to approve drugs based on evaluations of both the safety and the efficacy of the drug, as measured in clinical trials. Once the drug is on the market, a certain amount of additional "post-market" safety evaluation is required. Depending on the degree of risk associated with the drug, this may range from simple surveillance to specific additional studies, as determined by the regulatory agency.

Post-market safety studies are required because it is not possible to fully ascertain the safety of a drug in a controlled clinical trial. Clinical trials generally exclude groups of patients with serious diseases other than the one under study, since such patients would greatly complicate the interpretation of the results. Vulnerable groups such as children and pregnant women may also be excluded. However, all of these kinds of patients may be exposed to the drug once clinical trials are complete and it has been approved and is on the market. In addition, there is the possibility of evolving interaction with new drugs, or food, and lifestyle factors, which may not even exist at the time that the clinical trial is being performed. Drug interactions in general, and interactions between drugs and co-morbid conditions (e.g. worsening of diabetes in a diabetic cancer patient due to an anti-cancer drug), are of great concern in the field of pharmacovigilance.

Systems are in place for post-market pharmacovigilance, that is, the detection of safety signals from marketed drugs. A "safety signal" refers to a concern about an excess of adverse events compared to what would be expected if the occurrence of such events were independent of a drug's use. Regulatory agencies such as the FDA have established programs by which health care providers and patients can report adverse events to drug manufacturers and to the FDA itself. In some cases, these reports may be quite detailed, and may even include experimental re-challenge of a patient with a drug to check for reoccurrence of a non-serious adverse event, such as a rash. In this type of situation, a causal relationship between the drug and the adverse event does not need to rely on statistical techniques. However, in many cases, less detail is available. Reports are tallied into a table of Individual Safety Reports (ISRs), which generally include an approximate date of the event, the drugs that the patient was taking (very often more than one), and codes for the adverse event or events which occurred (also often more than one).

These ISRs are most often compiled into a matrix which indicates the prevalence of many possible drug-event combinations. Note that a complicating factor in using such data for pharmacovigilance is a lack of information about the size of the exposed population. With this type of data, pharmacovigilance methods generally rely on the detection of disproportionality of one drug-event combination compared to the rate at which the event occurs with other drugs. Data analysis methods which have been used with such data include the Multi-Item Gamma Poisson Shrinker (MGPS) [Du Mouchel, 2001; Szarfman 2002], the Proportional Reporting Ratio (PRR) method [Evans, 2001], and the Bayesian Confidence Propagation Neural Network (BCPNN) [Bate, 1998].

Deriving and tracking trends in pharmacovigilance data is an ongoing problem in view of the vast volume of data that needs to be analyzed together with the long timeframes over which much of this data is collected.

SUMMARY OF THE INVENTION

In certain aspects, the present invention relates to the visualization and detection of medically-important associations between drugs and adverse events, between different drugs, or between different adverse events (e.g., identification of syndromes), with or without the incorporation of relevant secondary data (e.g., demographic or clinical data).

In certain embodiments, the present invention provides a computer-implemented method of visualizing and analyzing a dataset of pharmacovigilance data, including: (a) determining a sample size-independent measure of association between two conditions of interest in the dataset of pharmacovigilance data; (b) determining a measure of statistical unexpectedness relating to the data on the relationship between the conditions of interest in said dataset, wherein the measure is based on an urn model under a hypothesis that the conditions are statistically independent; (c) visually displaying the measure of association with the measure of the statistical unexpectedness to aid in the determination of a significant association between the conditions of interest; and (d) tabulating the measures of association and of statistical unexpectedness to facilitate the generation of lists of conditions requiring further study.

In certain embodiments, the dataset comprises binary data and the measure of association comprises a reporting ratio $RR_{AB}$ defined as $$RR_{AB} = \frac{N_{AB}N}{N_A N_B},$$

where a total number of records in the dataset is N, a total number of records satisfying a first of the two conditions of interest is $N_A$, a total number of records satisfying a second of the two conditions of interest is $N_B$, and a total number of records satisfying both the first and second conditions of interest is $N_{AB}$.

In certain embodiments, the significant association between the two conditions of interest is determined if the following criteria are satisfied $RR_{AB} < 1$ and $C_{AB} = P\{N_{AB} \leq n\} < \theta$ $RR_{AB} > 1$ and $C'_{AB} = P\{N_{AB} \geq n\} < \theta$ where $\theta$ represents a small significance threshold probability for significance, $C_{AB}$ represents the cumulative probability ($C_{AB} = P\{N_{AB} \leq n\}$), and $C'_{AB}$ represents the complimentary probability $C'_{AB} = P\{N_{AB} \geq n\}$, wherein statistical unexpectedness ($U_{AB}$) of an observed response $N_{AB}$ is the reciprocal of the corresponding cumulative or complementary probability and defined as following $U_{AB} = 1/C_{AB}$ if $RR_{AB} < 1$ and $U_{AB} = 1/C'_{AB}$ if $RR_{AB} > 1$ In certain embodiments, the first condition of interest is a fixed reference condition, and the second condition of interest is range of relevant comparison conditions.

In certain embodiments the first condition of interest is a presence of a drug and the second condition of interest is an adverse event.

In certain embodiments, the reporting ratio or its logarithm is designated on the X-axis of a graph, and the statistical unexpectedness or its logarithm is designated on the Y-axis of the graph, and a point is plotted and labeled on the graph for each of a number of second conditions of interest.

In certain embodiments, a horizontal dotted line is plotted on the graph, designating a statistical significance threshold. For example, if it is desired to make a clear visual distinction for all first condition points corresponding to a statistical significance level of p=0.05, then the line is drawn at a Y-value corresponding to 20=1/0.05 on a log scale.

In certain embodiments, the significance threshold is adjusted for multiple comparisons wherein the significance threshold is adjusted using the Bonferroni correction wherein the significance threshold is adjusted to $\theta/M$ where M represents the number of comparisons between the first and second conditions of interest. Other corrections for multiple comparisons, besides the Bonferroni correction, may be used.

In certain embodiments, the step of displaying the measure of association includes separately indicating negative associations with reporting ratios less than one from positive associations with reporting ratios greater than one.

In certain embodiments, the present invention includes a preprocessing step in which the dataset is partitioned into subsets and then processing each subset of the dataset.

In certain aspects, the present invention provides a system for analyzing a dataset of pharmacovigilance data, including: an input unit for accessing the dataset of pharmacovigilance data; a processing unit configured for determining a sample size-independent measure of association between two conditions of interest in the dataset of pharmacovigilance data, and using a hypergeometric distribution to determine a measure of statistical unexpectedness between the conditions of interest in said dataset, wherein said distribution is based on an urn model under a hypothesis that said conditions are statistically independent; and a display unit for displaying the measure of association with the measure of the statistical unexpectedness to identify a significant association between the conditions of interest.

In certain embodiments, the present invention provides a computer program product on a computer readable medium that, when executed on a computing system, analyzes a dataset of pharmacovigilance data, the program product including: code for determining a sample size-independent measure of association between two conditions of interest in the dataset of pharmacovigilance data; code for using a hypergeometric distribution to determine a measure of statistical unexpectedness between the conditions of interest in said dataset, wherein said distribution is based on an urn model under a hypothesis that said conditions are statistically independent; and code for displaying the measure of association with the measure of the statistical unexpectedness to identify a significant association between the conditions of interest.

DETAILED DESCRIPTION OF THE PREFERRED EMBODIMENTS

In view of some of the problems discussed earlier herein, techniques that improve deriving and tracking trends in pharmacovigilance data are of utmost importance so that, for example, adverse events caused by particular drugs can be discovered as soon as possible. Likewise, discovering positive associations, such as the unexpected beneficial effects of a drug to reduce the certain adverse events are also very valuable because these drugs may then be used for therapeutic purposes, or to reduce the number of adverse events in the future.

The ultimate goal of pharmacovigilance is the assessment of causality in drug-adverse event relationships, and this is not an entirely objective statistical exercise. Medical judgment and human pattern recognition currently play a significant role. Consequently, a pharmacovigilance tool does not necessarily need to make fully-automated decisions about the safety of drugs, or even attempt to create a one-dimensional ordered list of drugs based on their level of risk. A useful tool is one which presents drug-safety data in a visual manner which facilitates or improves expert medical judgment and decision-making. The role of the computer in such a system is to summarize an extremely large amount of data into a presentation of information that can be readily understood, and which accurately represents the statistical features and trends of the data for both large and small numbers of adverse events. This is the design philosophy embodied in the several embodiments of the present invention.

In certain embodiments, the present invention presents a computer implemented computational procedure that generates, from a given dataset D, a set of numbers useful in characterizing pairs of Conditions of Interest, described further herein, together with a display (such as a two-dimensional graphical display) to aid in interpreting these results (or numbers). In the example of displaying the results as a two dimensional graphical display, the horizontal axis of this graph is defined by an association measure, such as one previously used in pharmacovigilance studies, that is not sensitive to sample size effects. The vertical axis is based on the probability of the observed response under a statistical independence model, a quantity that is strongly dependent on sample size effects. Regions of this plot or display can be identified that correspond to unexpectedly strong positive associations (which may be due to harmful drug interactions or other undesirable phenomena), unexpectedly strong negative associations (which may be due to beneficial drug effects or to prescribing patterns like nonprescription of certain drugs for pregnant women), and results that are probably not of interest (e.g., associations that are not strong and/or not statistically significant).

Figure 1:
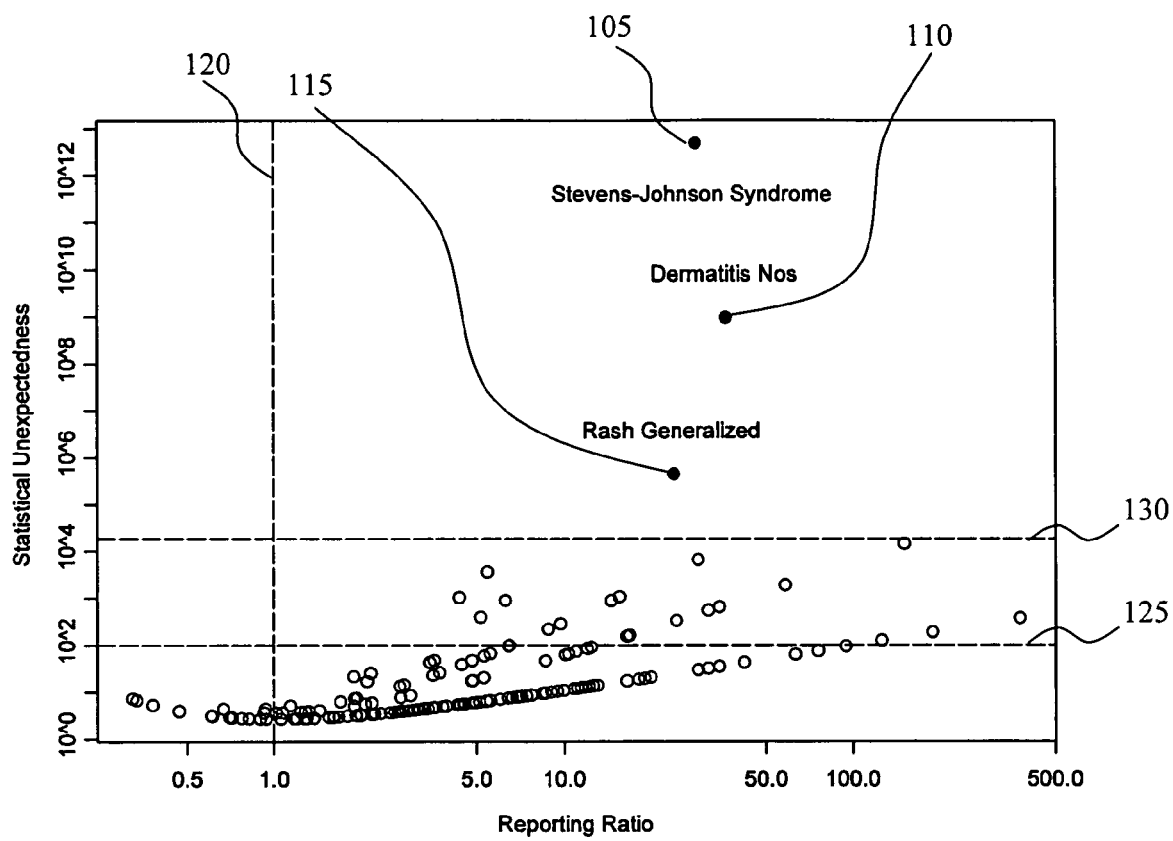
FIG. 1 is a diagram that illustrates a plot of phamacovigilance data with a Reporting Ratio on one axis and a measure of statistical unexpectedness on the other axis in one embodiment of the present invention.

FIG. 1 discloses an example plot according to one embodiment of the present invention that summarizes results obtained from the FDA's Adverse Event Reporting System (AERS) database, for the second quarter of 2002. It should be recognized that FIG. 1 is exemplary only. One skilled in the art would recognize various modifications and alternatives all of which are considered a part of the present invention. In this example, Condition A (a first condition of interest) corresponds to the drug BEXTRA® and the Comparison Conditions B (second condition of interest) considered are all adverse reactions that appear in one or more event reports together with the drug BEXTRA®. The three adverse reactions showing the greatest statistical unexpectedness (reciprocal of the probability of observing this result under the statistical independence model) are labeled as points 105, 110, and 115 in the plot. The vertical line 120 corresponds to a Reporting Ratio of 1, the value indicative of no association between the drug and the adverse events (i.e., the two conditions of interest). The two horizontal lines 125 and 130 correspond to an uncorrected 1% significance limit (the lower line 125) and a 1% significance limit (the upper line 130) corrected for multiple comparison effects, using the Bonferroni correction, explained further herein. Points (105, 110, and 115) whose statistical unexpectedness exceeds this Bonferroni limit are marked with solid circles and, in this particular example, labeled with the name of the corresponding adverse reaction (Rash, Dermatitis, and Stevens-Johnson Syndrome, respectively). This data plot suggest an association between BEXTRA® and skin conditions, including the one known as Stevens-Johnson Syndrome as shown by point 105.

Figure 2:
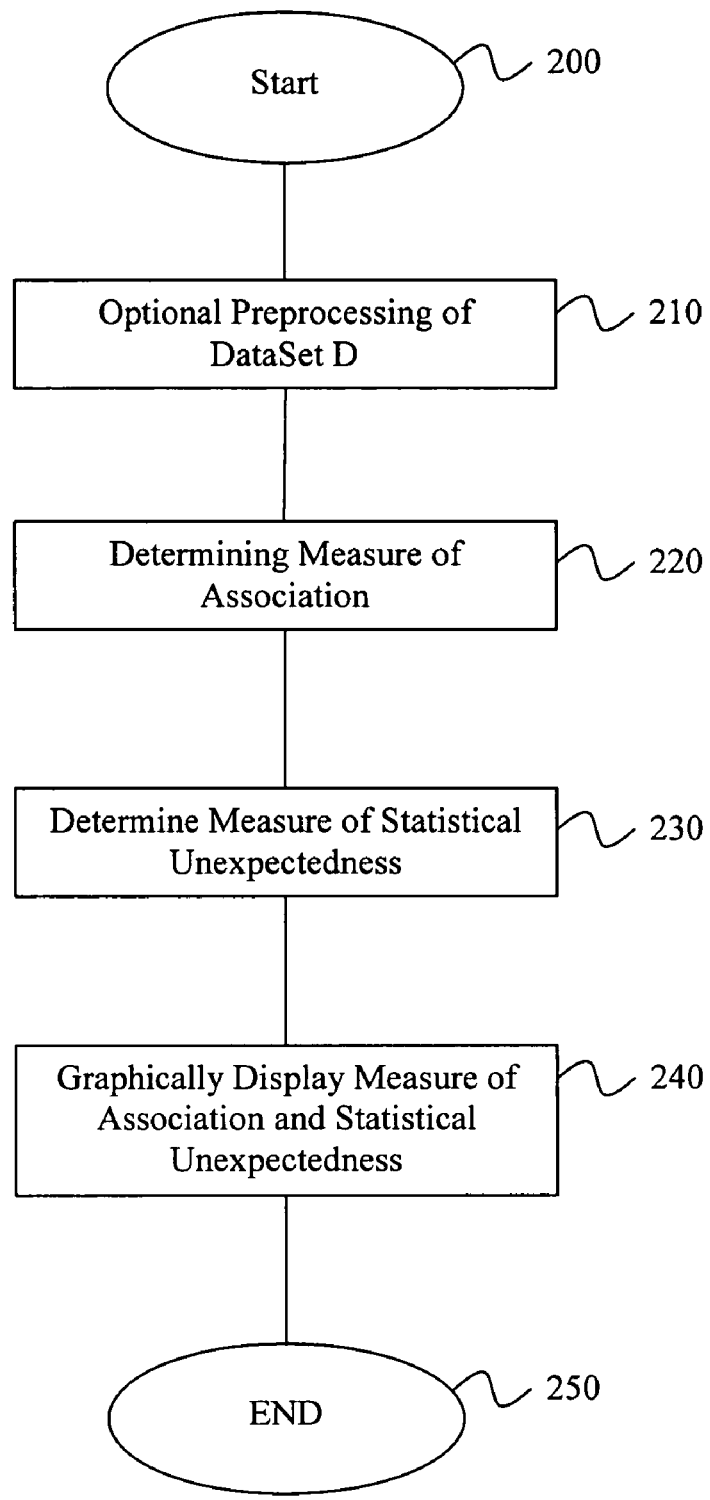
FIG. 2 is a flowchart that illustrates the process steps in one embodiment of the present invention.

FIG. 2 illustrates the process steps that implement certain embodiments of the present invention. For a given dataset of pharmacovigilance data (for example, adverse event data from a government agency or a private data source), an optional preprocessing step 210 may be performed. This preprocessing step 210 selects subsets of the given dataset so that the subsequent analysis discussed herein may be performed on one or more of the subsets. Details of the optional preprocessing step 210 are provided further herein. In step 220, the process determines a measure of association between two conditions of interest (on the entire dataset or on one or more subsets of the dataset if the preprocessing step has been performed). Further details of the process of determining the measure of association are provided further herein. In step 230, a measure of statistical unexpectedness is determined for the observed association between the two condition of interest (for example, between an adverse event and a drug). Finally, in step 240, the determined measures of association and statistical unexpectedness are displayed so that interesting or significant associations (or absence thereof) can be easily observed.

In certain embodiments, an assumption underlying the present invention is described using the following data model: The given dataset D is assumed to consist of N records, each consisting of the following fields:

1. one or more drugs $d_i$
2. one or more adverse reactions $r_j$
3. zero or more additional fields containing other information (e.g., demographic data, clinical data, etc.)

In certain embodiments, the method described here characterizes the relationship between pairs of Conditions of Interest, defined as collections of records that satisfy one of the following conditions:

1. each record lists a specified drug $d_i$
2. each record lists a specified adverse reaction $r_j$
3. each record lists a drug or reaction in conjunction with specified information from the additional fields (e.g., a specified drug for female patients or a specified reaction among patients in a particular age range),
4. any other combination of drug, adverse reaction, and additional information (such as demographic information) from the dataset D that uniquely defines a set of records.

The graphical display generated by the procedure described herein is based on the results obtained for a single Reference Condition of Interest (Condition A) and a family of Comparison Conditions of Interest (i.e., a set of Conditions B). As an illustrative example, taking the Reference Condition as a specific drug of interest, a useful set of Comparison Conditions is a set of all adverse events appearing in one or more records listing the drug of interest. More generally, Comparison Conditions B can be any well-defined set of Conditions of Interest, as defined above, whose possible association with Condition A is of interest. In certain embodiments, it is assumed that all Comparison Conditions B have at least one record in common with Reference Condition A (i.e., that $N_{AB} \geq 1$), but one advantage of the method discussed herein is that it extends naturally to the case of non-coincident conditions (i.e., cases where $N_{AB}=0$).

The following paragraphs first describe the analysis performed for the Reference Condition with each individual member of the set of Comparison Conditions. Then a graphical display constructed from all results in the set of Comparison Conditions is described.

Given two conditions of interest, Condition A and Condition B, the following two binary sequences are defined for every record in dataset D:

$a_k=1$ if Record $R_k$ satisfies Condition A, and $a_k=0$ otherwise, $b_k=1$ if Record $R_k$ satisfies Condition B, and $b_k=0$ otherwise.

Quantitative measures of association between Conditions A and B can be defined in many different ways. See, for example, Agresti [Agresti, 2002], the relevant disclosure of which is incorporated herein. Most of these measures of association depend on the following four integers:

1. the total number of records N in dataset D,
2. the total number of records $N_A$ satisfying Condition A,
3. the total number of records $N_B$ satisfying Condition B,
4. the total number of records $N_{AB}$ satisfying both Conditions A and B.

Note that these numbers define the following 2×2 contingency table:

|       | A             | Not A                      | Total     |
|-------|---------------|----------------------------|-----------|
| B     | $N_{AB}$      | $N_B - N_{AB}$             | $N_B$     |
| Not B | $N_A - N_{AB}$| $N - N_A - N_B + N_{AB}$   | $N - N_B$ |
| Total | $N_A$         | $N - N_A$                  | N         |

These numbers are related to the binary sequences $\{a_k\}$ and $\{b_k\}$ via the following simple expressions:

$$N_A = \sum_{k=1}^{N} a_k \quad N_B = \sum_{k=1}^{N} b_k \quad N_{AB} = \sum_{k=1}^{N} a_k b_k \qquad (1)$$

In certain embodiments, the relationship between Conditions A and B are characterized with two numbers, both derived from the four numbers $N_A$, $N_B$, $N_{AB}$, and N defined above: (1) a traditional measure of association, and (2) a measure of statistical unexpectedness based on the probability of observing these four numbers under a null hypothesis that Conditions A and B are statistically independent.

The following paragraphs describe the details of determining a measure of association between two conditions of interest in step 220. Of the many available association measures between two binary sequences, the following three are described in the pharmacovigilance literature:

1. the Reporting Ratio $$RR_{AB} = \frac{N_{AB} N}{N_A N_B},$$

2. the Proportional Reporting Ratio $$PRR_{AB} = \frac{N_{AB}(N - N_A)}{N_A(N_B - N_{AB})},$$

3. the Report Odds Ratio $$ROR_{AB} = \frac{N_{AB}(N - N_A - N_B + N_{AB})}{(N_A - N_{AB})(N_B - N_{AB})}.$$

Unfortunately, the terminology used in the literature is not entirely standard. For example Gould [Gould, 2003] defines the first of these three measures as the "proportional reporting ratio," while Du Mouchel [Du Mouchel, 1999] defines this first measure as the "nonstratified relative report rate." The definition of "proportional reporting ratio" used herein is defined in Heeley [Heeley, 2002]. Gould cites a reference arguing that the Report Odds Ratio defined above has better resistance to the effects of under-reporting than the Reporting Ratio, but both the Report Odds Ratio and the Proportional Reporting Ratio as defined here suffer from the fact that their value becomes infinite when $N_B=N_{AB}$, and the Report Odds Ratio is also infinite whenever $N_A=N_{AB}$. This observation is important because both of these situations can and do arise in the analysis of pharmacovigilance data. For these reasons, the use of Reporting Ratio as defined above is advantageous in certain embodiments of the present invention. Finally, it should be noted that all of these association measures are invariant under a common rescaling of all counts by any constant multiplier.

The following paragraph discusses some of the processing performed in determining a measure of statistical unexpectedness in step 230. In certain embodiments, the statistical unexpectedness measure included in the method described herein is based on the idea of comparing the observed results with a random reference model. That is, under the assumption that Conditions A and B are not associated, the two sequences $\{a_k\}$ and $\{b_k\}$ should be statistically independent. It is possible to compute the probability $p_{AB}$ of observing the number $N_{AB}$ of simultaneous occurrences of Conditions A and B under this independence assumption, given the observed values for $N_A$, $N_B$, and N. This point is important because, unlike other methods (e.g., the GPS method described by DuMouchel 1999), the method described herein does not impose any distributional assumptions on the data values. This independence from distributional assumptions is a significant practical advantage, both because errors in specification of the data distribution in methods requiring distributional assumptions can cause those methods to perform poorly, and because changes in the original application scenario for those methods can require modifications of these distributional assumptions.

To compute the probability $p_{AB}$, the method proceeds as follows. First, it should be noted that since the summation index k in sequence $\{a_k\}$ is arbitrary, nothing is changed by re-ordering these sums, defining a new summation index l such that $a_l=1$ for $l=1,2,\ldots,N_A$ and $a_l=0$ for $l=N_A+1, N_A+2,\ldots,N$ Under this new labeling, the value of $N_{AB}$ is given by $$N_{AB} = \sum_{l=1}^{N} a_l b_l = \sum_{l=1}^{N_A} b_l$$

The advantage of this expression is that it converts the statistical independence assumption into the following urn model: Consider the dataset D as an urn containing N balls, of which $N_A$ are white and the remaining $N-N_A$ are black. Under the statistical independence hypothesis, the $N_B$ records satisfying Condition B may be regarded as a random sample of $N_B$ balls drawn from the urn, of which $N_{AB}$ are white. It is a standard result that the probability of observing $N_{AB}=n$ is given by the hypergeometric distribution:

$$p_{AB} = P\{N_{AB} = n\} = \frac{\binom{N_A}{n}\binom{N-N_A}{N_B-n}}{\binom{N}{N_B}}$$

for $\max\{0, N_A+N_B-N\} \leq n \leq \min\{N_A, N_B\}$

The urn model is described in detail by Johnson [Johnson, 1992].

It should be noted that in typical pharmacovigilance applications, $N_A + N_B \ll N$, so the lower limit on n is zero. It should be noted that expected value of $N_{AB}$ under this independence model is:

$$E\{N_{AB}\} = \frac{N_A N_B}{N}$$

as explained in [Johnson, 1992].

Note that if $N_{AB}$ is equal to this expected value, the Reporting Ratio is equal to 1:

$$N_{AB} = E\{N_{AB}\} \Rightarrow RR_{AB} = \frac{N_{AB}N}{N_A N_B} = \frac{N_{AB}}{E\{N_{AB}\}} = 1$$

The practical importance of this observation lies in the fact that detection of significant associations involves the identification of Conditions A and B that have low probability under the statistical independence model. The hypergeometric distribution is unimodal, so small probabilities occur in the tails of the distribution. Hence, if the Reporting Ratio is less than 1, significant values of $N_{AB}$ fall in the left tail of the distribution, while if the Reporting Ratio is greater than 1, significant values of $N_{AB}$ fall in the right tail of the distribution. This observation leads to the following selection criteria for statistically unusual associations (i.e., associations that are inconsistent with the independence null hypothesis):

$$RR_{AB} < 1 \text{ and } C_{AB} = P\{N_{AB} \leq n\} < \theta \quad 1.$$

$$RR_{AB} > 1 \text{ and } C'_{AB} = P\{N_{AB} \geq n\} < \theta \quad 2.$$

Here, θ represents a small threshold probability for significance (e.g., θ=0.01 corresponds to a 1% significance threshold). The cumulative probability $C_{AB}=P\{N_{AB} \leq n\}$ is easily computed using standard procedures. For example, the S-Plus® statistical software package (Insightful Corp., Seattle, Wash.) contains built-in procedure phyper which computes this probability. The complimentary probability $C'_{AB}=P\{N_{AB}>n\}$ can, in principle, be computed using this function and the following result, provided n>0:

$$P\{N_{AB} \geq n\} = 1 - P\{N_{AB} < n\} = 1 - P\{N_{AB} \leq n-1\}$$

This procedure performs extremely poorly in practice, however, due to round-off problems: small differences between much larger numbers can be highly inaccurate. A much better alternative proposed herein takes advantage of the relations between cumulative probabilities described by Johnson, which provides a basis for computing $C'_{AB}$ using cumulative distribution function routines (e.g., the phyper built-in function in S-plus) with modified arguments.

In the procedure described here, the statistical unexpectedness of the observed response $N_{AB}$ is defined as the reciprocal of the appropriate cumulative probability:

$$U_{AB}=1/C_{AB} \text{ if } RR_{AB}<1 \text{ and } U_{AB}=1/C'_{AB} \text{ if } RR_{AB}>1$$

Since pairs of conditions that are inconsistent with the statistical independence hypothesis are those with small associated cumulative probabilities, the statistical unexpectedness measure defined here will be large for these pairs of conditions. In particular, it should be noted that $U_{AB} \geq 1$ in all cases, but this quantity is unbounded above.

In certain embodiments, the basic pharmacovigilance tool proposed herein is inspired by the "volcano plot," commonly used to present microarray data analysis results as described by Wolfinger [Wolfinger, 2001]. In Wolfinger 2001, a measure of signal strength (specifically, the differences between two mean responses) is plotted against the p-value associated with a t-test of the hypothesis that the two means are equal. These values are plotted for each of a large number of genes characterized by the microarray experiment, and "interesting" genes are generally regarded as those exhibiting a sufficiently large difference in means (i.e., a strong enough signal) and sufficiently small t-test p-values (i.e., statistical significance at a specified level). In sharp contrast to the disclosure of Wolfinger 2001, in the method described here (which is exemplary of the processing that may be performed in step 240 of FIG. 2), the statistical unexpectedness $U_{AB}$ is plotted against the Reporting Ratio $RR_{AB}$ for a fixed Reference Condition A and a range of relevant Comparison Conditions B. It should be noted that this display (as shown in FIG. 1) is exemplary only of one type of display. One skilled in the art would recognize that various other displays (involving statistical unexpectedness and reporting ratio) may be used and all such displays are considered as a part of the present invention.

Heeley 2002 describes a pharmacovigilance-related plot of probability versus a measure of association which differs from certain embodiments of this invention in at least three respects. First, Heeley 2002 uses the Proportional Reporting Ratio defined earlier in this document, which is infinite when $N_B=N_{AB}$, as noted earlier. Second, instead of statistical unexpectedness, these authors use Yates' continuity-corrected $\chi^2$ values computed from a test of statistical independence. The original $\chi^2$ statistic was proposed in 1900 by Karl Pearson, who derived its distribution for large samples, and Yates proposed his correction in 1934 as a computationally simpler approximation to Fisher's exact test, which is based on the hypergeometric distribution. Johnson 1992 notes that the approximate p-values associated with this corrected $\chi^2$ statistic are "appropriate for large $N_B$, provided $N_A/N$ is not too small." This condition is frequently violated in the phamacovigilance applications considered here and therefore provides another reason why the plot of Heeley 2002 would not work well with the pharmacovigilance applications considered herein. More generally, the article by Mielke [Mielke, 2001] argues against the use of the $\chi^2$ statistic in problems like the one considered herein that are equivalent to tests of independence in a 2×2 contingency table. Specifically, these authors note that:

It is well known that when expected cell frequencies are small, probability values based on the asymptotic $\chi^2$ probability distribution may be erroneous . . . .

These authors further note that the quality of the $\chi^2$ approximation depends on the following four problem characteristics:

1. the sample size (here, N),
2. the marginal probabilities (here, $N_A$ and $N_B$),
3. the number of cells in the two-way contingency table (here, 4), and
4. the significance level.

These observations are important since in the pharmacovigilance applications considered herein, while N is typically quite large, relevant values of $N_A$ and $N_B$ often cover a very wide range. Also, it should be noted that the $\chi^2$ approximation can be expected to degrade increasingly as we move further into the tails of the distribution, corresponding to small probabilities or large statistical unexpectedness values. This behavior is particularly undesirable since it precisely these values that are of greatest interest in the pharmacovigilance application considered in the present invention.

Finally, a third important difference between the approach described herein in certain embodiments of the present invention and that of Heeley 1993 is that the method described herein adopts a correction for multiple comparisons. See generally Westfall [Westfall, 1993]. Specifically, it should note that the identification of Condition A/B pairs with "large statistical unexpectedness values" corresponds to a rejection of the hypothesis of statistical independence between Conditions A and B. For a fixed significance level θ, the probability of erroneously rejecting the independence hypothesis for any individual pair is θ, but the probability of erroneously rejecting the independence hypothesis for at least one of M distinct comparisons is larger than θ. Indeed, if all of the comparisons are statistically independent, this probability could be on the order of Mθ. One popular solution to this problem is the Bonferroni approximation, which replaces the original significance threshold value θ with the modified value θ/M. While the Bonferroni correction is known to be conservative [Westfall 1993], it has the advantage of simplicity and is incorporated into the procedure described herein in certain embodiments. Alternatively, other corrections for multiple comparisons may also be used as described in, for example, Westfall 1993, the relevant disclosure of which is incorporated herein. Specifically, the pharmacovigilance plots described herein include two horizontal reference lines (for example, the lines 125 and 130 in FIG. 1) to aid in identifying the results of greatest interest: one corresponding to a 1% threshold, at an unexpectedness value of U=1/0.01=100, and a second one corresponding to the Bonferroni-corrected 1% significance threshold, at U=100M. Interesting Comparison Conditions B are generally defined as those for which the unexpectedness $U_{AB}$ exceeds this Bonferroni-corrected threshold. One skilled in the art would recognize that the 1% threshold discussed herein is exemplary only and other significance thresholds could also be used which are also considered a part of the present invention.

Typically, pharmacovigilance methods focus on positive associations between two conditions of interest, often explicitly excluding the case of negative associations from consideration (e.g., DuMouchel 1999). An advantage of the method described here is that it assesses both positive and negative associations in the same plot. Specifically, note that significant negative associations correspond to Reporting Ratios less than 1 and high statistical unexpectedness, while significant positive associations correspond to Reporting Ratios greater than 1 with high statistical unexpectedness. To separate these two regions, a vertical line is included in the plot considered here at $RR_{AB}$=1 (for example, line 120 in FIG. 1). In addition, the method described herein provides a basis for assessing absent associations which represents the most extreme form of negative association. Specifically, consider the case where $N_z$ Comparison Conditions B are potentially of interest but exhibit no overlap with the Reference Condition A. This case corresponds to $N_{AB}$=0, for which the hypergeometric probability is given by (See Johnson 1992 at page 262):

$$p_z = P\{N_{AB} = 0\} = \frac{(N - N_A) \cdots (N - N_A - N_B + 1)}{N \cdots (N - N_B + 1)} = \left(1 - \frac{N_A}{N}\right) \cdots \left(1 - \frac{N_A}{N - N_B + 1}\right)$$

In the case considered here, both the dataset D and Condition A are fixed, meaning that both N and $N_A$ are fixed. Under these conditions, note that $p_z$ is a monotonically decreasing function of $N_B$, bounded above by:

$$p_z \leq \left(1 - \frac{N_A}{N}\right)^{N_B}$$

Hence, the absence of some Comparison Condition B is significant at the level θ if $p_z$ is less than θ, which is true if the following condition holds:

$$\left(1 - \frac{N_A}{N}\right)^{N_B} < \theta \Rightarrow N_B \ln\left(1 - \frac{N_A}{N}\right) < \ln \theta \Rightarrow N_B > \frac{\ln \theta}{\ln\left(1 - \frac{N_A}{N}\right)}$$

It should be noted that since the arguments of the logarithms are less than 1, the logarithms are negative; and this is why the direction of inequality was reversed in the last step above. While this condition is only sufficient for $p_z<\theta$, and therefore conservative, the approximation is quite good when $N_B \ll N$, as is typically the case in most pharmacovigilance data of interest. As discussed earlier herein, a simple correction for multiple comparisons in this problem is to replace the threshold θ with the Bonferroni-corrected threshold $\theta/N_z$. The practical significance of this result is that it gives a good approximation to the number of records satisfying Condition B required for a complete absence of records satisfying Conditions A and B together to be significant. One application for this result is the detection of potentially beneficial drug effects that lead to fewer occurrences of a particular adverse event than expected by random chance. Another possible application is the detection of fraud (e.g., deliberate under-reporting of a particular adverse event).

Variations in the Choice of Conditions

In the example shown in FIG. 1 and elsewhere, the first condition, which corresponds to the graph, is the presence of the drug BEXTRA®, and the second conditions, which correspond to the points on the graph, are adverse event codes. Additional variations are possible, and have various uses in the practice of pharmacovigilance as discussed in the following paragraphs.

Figure 4:
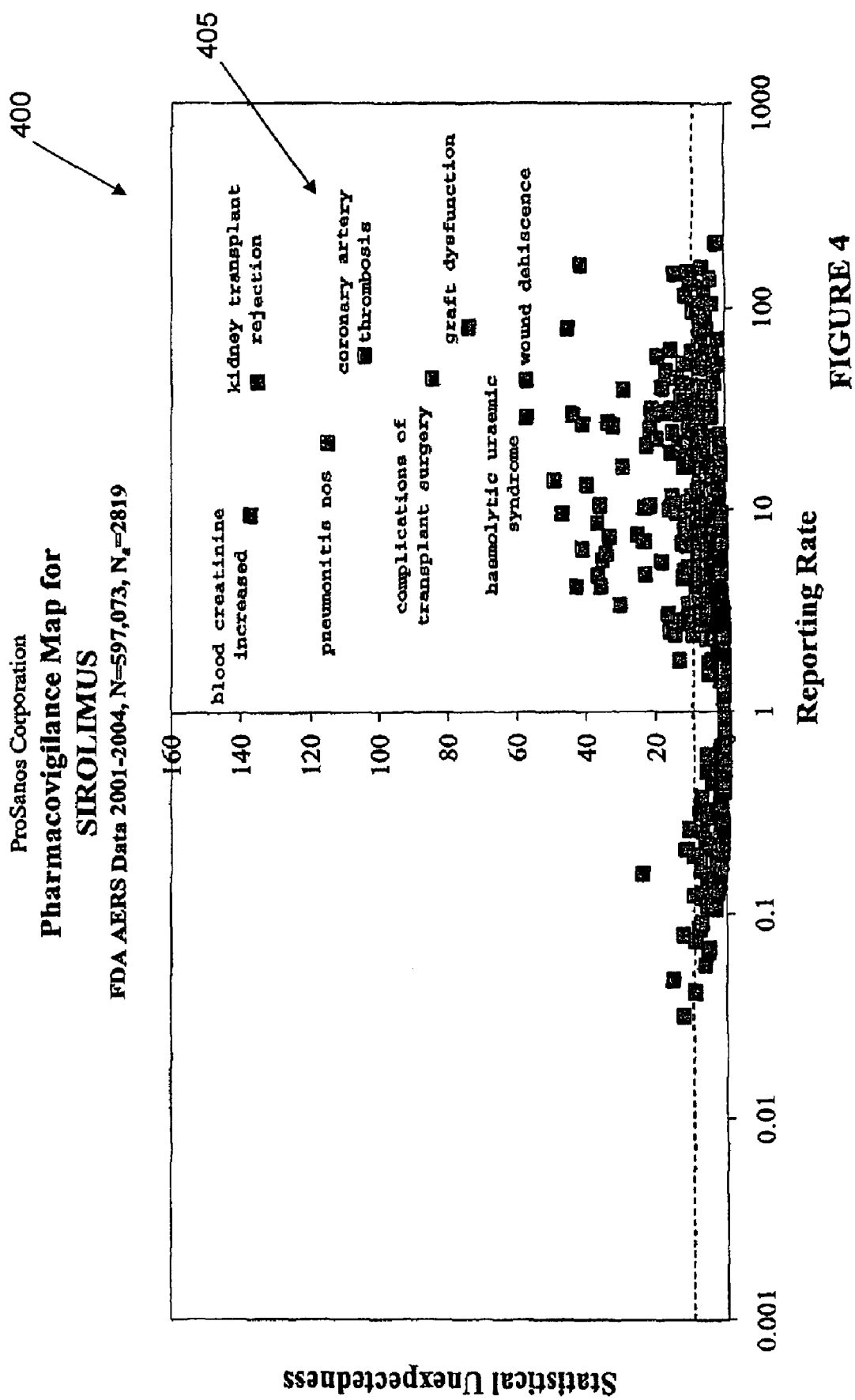
FIG. 4 is a display of a basic pharmacovigilance map for the drug SIROLIMUS.

FIG. 4 illustrates another pharmacovigilance map 400, this one for the drug SIROLIMUS. It is noted that a number of adverse event codes 405 appear in the upper right portion of this graph, which an investigator may wish to study further in connection with this drug. In that investigation, it may be desirable to know which drugs, among all drugs, are most strongly associated with the adverse effect of interest, for example, the adverse event known as "wound dehiscence".

Figure 5:
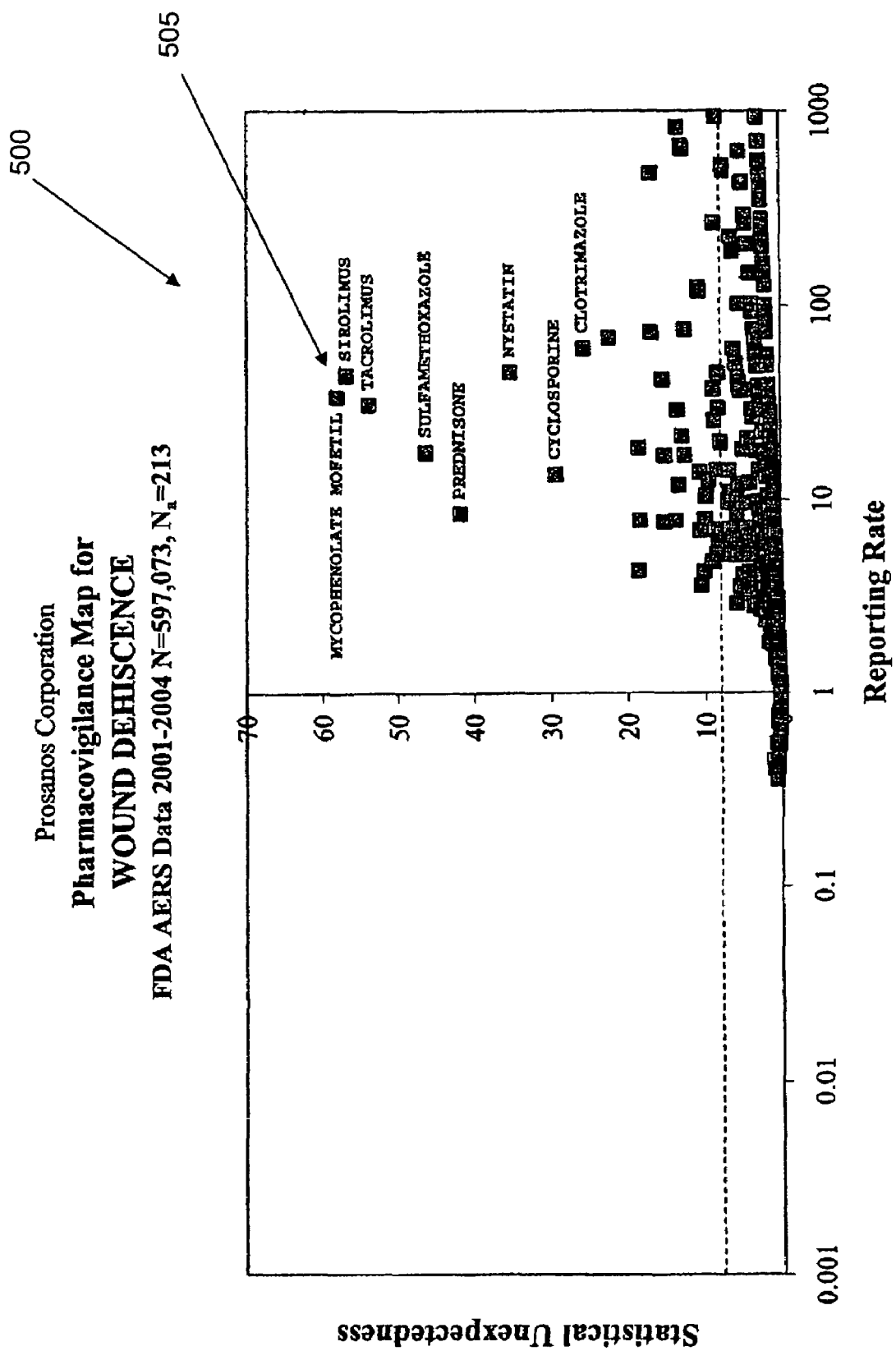
FIG. 5 is a display of a basic pharmacovigilance map for the adverse event WOUND DEHISCENCE.

In a useful variation of the pharmacovigilance map 500, as shown in FIG. 5, the graph (first condition) corresponds to a particular adverse event code, and each point (second condition) corresponds to a drug. From such a map 500, a investigator would note that the drug SIROLIMUS is one of the drugs most strongly associated with the adverse event known as "wound dehiscence", due to the appearance of the data point 505 for SIROLIMUS in the upper right corner of the map 500.

In another useful variation, the graph corresponds to a particular pair of drugs taken together by a patient, and each point corresponds to an adverse event. This form of graph can be used to ascertain whether any significant drug interactions exist between the pair of drugs under study.

In another useful variation, the graph (first condition) corresponds to a combination of a drug and adverse event occurring together, and each point corresponds to a second drug also taken by the patient. This form of graph can be used to ascertain which drugs might be responsible for a suspected drug interaction that causes the particular adverse event.

In another useful variation, the graph corresponds to a particular drug, and each point corresponds to a second drug taken in combination with the first drug. This form of graph can provide background information for pharmacovigilance investigations, by indicating what drugs are most commonly taken along with a drug under investigation.

In another useful variation, the graph corresponds to a particular adverse event, and each point corresponds to a second adverse event which occurs along with the first one. This form of graph is useful for the detection and investigation of syndromes, which are combinations of symptoms (adverse events in this case) which occur together. Syndromes can be indicative of causal relationships between drugs and adverse events.

Many further variations in the designation of first condition (defining the graph) and second condition (defining the points) are possible, for example, to investigate three-way drug interactions. These are all considered within the scope of this invention.

Advantages/Improvements of Certain Embodiments

Relative to the Gamma Poisson Shrinker (GPS) procedure of DuMouchel and the Bayesian Confidence Propagation Neural Net (BCPNN) procedure of Bate, commonly-used methods in pharmacovigilance, one advantage of certain embodiments described here is the use of two distinct characterizations for each pair of Conditions of Interest, (1) a sample-size independent association measure like the Reporting Ratio together with (2) a statistical unexpectedness measure under a null hypothesis of statistical independence, rather than a single score for each condition. In producing a single score, loss of separate information about disproportionality and statistical significance occurs. This makes it more difficult to visualize the data and analyze it in a manner that allows for expert human judgment in the medical interpretation of pharmacovigilance data.

A second advantage of certain embodiments relative to the above-referenced known procedures is the much weaker statistical assumptions on which the certain embodiments are based. Specifically, the certain embodiments are based on the assumption that all records satisfying a particular Condition of Interest are equivalent (i.e., exchangeable), and the null hypothesis considered is one of statistical independence between Conditions of Interest. No data distributions need be specified in this method, in contrast to methods like GPS, for which underlying data distributions are specified as discussed in DuMouchel 1999.

A third advantage of the method described herein is simplicity: the basic mechanics of the urn model formulation can be easily explained to medical and pharmaceutical personnel with limited statistical backgrounds, in contrast to methods like MGPS that are based on Bayesian statistics.

A fourth advantage over both the previously-referenced methods and the simple Proportional Reporting Ratio (PRR) of Evans is the ability to properly visualize and draw implications from the occurrence of zero to four events. Methods utilizing the chi-squared distribution are not valid below five events. The Bayesian methods referenced above avoid this limitation through a complex procedure based on strong statistical assumptions. These methods do not produce valid results for zero events.

Some of the features in certain embodiments of the present invention include the following:

1. The formulation of pharmacovigilance problems in terms of statistical urn models. This leads to a simple statistical model which does not require strong distributional assumptions.
2. The use of statistical unexpectedness (the reciprocal of probability derived from a statistical independence model) in pharmacovigilance applications.
3. The use of statistical unexpectedness together with a traditional association measure like Reporting Ratio to characterize pharmacovigilance results.
4. The use of corrections for multiple comparison (for example, Bonferroni bounds) in screening relatively large collections of pharmacovigilance results.
5. The detection of statistically significant absent conditions (i.e., cases where $N_{AB}=0$ is observed but is inconsistent with a statistical independence model).

Adaptation to Clinical Trial and Medical-Record Safety Data

For pharmacovigilance data derived from a spontaneous-reporting system such as AERS, the horizontal axis of the graphs produced by certain embodiments represents the Proportional Reporting Rate (PRR) or optionally an Odds Ratio (OR). Drug-safety data from a clinical trial may also be visualized and analyzed using certain of the embodiments disclosed herein. In this case, the available data for each adverse event type consists of: $n_D$, the number of patients experiencing the adverse event while taking the study drug D; $N_D$, the total number of patients in the study taking drug D; $n_P$, the number of patients experiencing the adverse event while taking a placebo; and $N_P$, the total number of patients in the study taking a placebo. It is possible that the study contains multiple arms and involves multiple drugs and doses, but the principles described here hold in those cases. In place of the PRR, certain embodiments can be practiced using the Relative Risk ($\zeta$) of an adverse reaction for the drug vs. placebo:

$$\zeta = \frac{n_D/N_D}{n_P/N_P},$$

or the Odds Ratio (OR)

$$OR = \frac{n_D/(N_D - n_D)}{n_P/(N_P - n_P)}.$$

Under the null hypothesis, $\zeta = OR = 1$. Statistical unexpectedness can be calculated based on an urn model which essentially says that the placebo urn and the drug urn contain the same proportion of black balls. In other words, $$p_D = P\{n_D = n\} = \frac{\binom{N_D}{n}\binom{N_P}{n_P}}{\binom{N_D + N_P}{n + n_P}}.$$

This corresponds to Fisher's Exact Test for a 2×2 table. While this statistical test is well known, certain embodiments disclosed herein describe methods of utilizing it to visualize drug safety data in a number of variations. The utility of this may include side-by-side visual comparison of pre-market clinical trial safety data, and post-market, spontaneously-reported safety data as described above.

In some cases, drug-safety data is derived from patient medical records. In this case, the available data consists of: $n_D$, the number of patients experiencing the adverse event within a given time interval while taking a drug of interest D; $N_D$, the total number of patients in the medical-records database taking drug D within a given time interval; $n_X$, the number of patients experiencing the adverse event within the given time interval while not taking drug D; and $N_X$, the total number of patients in the study taking a placebo. Relative Risk, Odds Ratio, and statistical unexpectedness can be calculated as for clinical trial data, and visualized according to the methods of this invention. This can facilitate the side-by-side visual and analytic comparison of: 1) Pre-market safety data from clinical trials; 2) Post-market active surveillance data determined by examining a set of patient medical records; 3) Post-market passive surveillance data from a spontaneous-reporting system such as the FDA AERS system.

Additional Embodiments

The basic method described thus far starts with a fixed dataset D. In certain embodiments, a preprocessing step is provided (as shown in step 210 of FIG. 2) that decomposes this dataset into subsets, based on any of the following criteria:

1. fixed-size moving-window partitioning based on either a record index or on auxiliary information like reporting date:
   a. $W_k = \{R_{k-K}, \ldots, R_k, \ldots, R_{k+K}\}$ for each individual record k from k=K+1 to k=N−K where the window half-width K is fixed 2. nearest-neighbor partitioning based on any auxiliary variable X (e.g., reporting date or patient age) to which a distance function d(•,•) can be applied:
   a. $W_k = \{R_j | d(X_j, X_k) < \alpha\}$ for each individual record k where $\alpha$ is a specified neighborhood radius 3. cluster-based partitioning based on any standard cluster analysis method like those described by Gordon [Gordon, 1999], the relevant disclosure of which is incorporated herein.

4. stratification-based partitioning, in which the dataset is subdivided into disjoint subsets (strata) in which one or more auxiliary variables belong to a specified subset (e.g., all records corresponding to male vs. female patients, all records within specified patient age ranges, etc.)

In all of these additional embodiments, the basic analysis procedure described here is applied separately to each partition of the dataset D. One advantages of this partitioning is a relaxation of the exchangeability assumptions from global (i.e., all records satisfying the Conditions of Interest in the dataset are exchangeable) to local (i.e., all records satisfying the Conditions of Interest in each subset are exchangeable with other records in the subsets). This permits the detection and treatment of violations of global exchangeability assumptions like time-trends, local bursts of reporting activity (for example, following news reports of suspected drug reactions), or other forms of non stationary data or data inhomogeneity. A second advantage of this partitioning is the ability to compare across partitions to detect systematic dependencies on partitioning criteria. In addition, by comparing results from stratification-based partitioning with those for the complete dataset, it is possible to detect Simpson's paradox, in which associations differ strongly (e.g., reverse direction) between stratified and non-stratified data. See Agresti [Agresti, 2002]. Detection of Simpson's paradox is potentially useful because a necessary condition for its occurrence is a sufficiently strong association between the Conditions of Interest and the stratification variables. See Schield [Schield, 1999]. The identification of these associations can be useful in detecting possibly important confounding influences (e.g., gender-specific drug interactions).

Construction of Confidence Boxes for Certain Points

Figure 6:
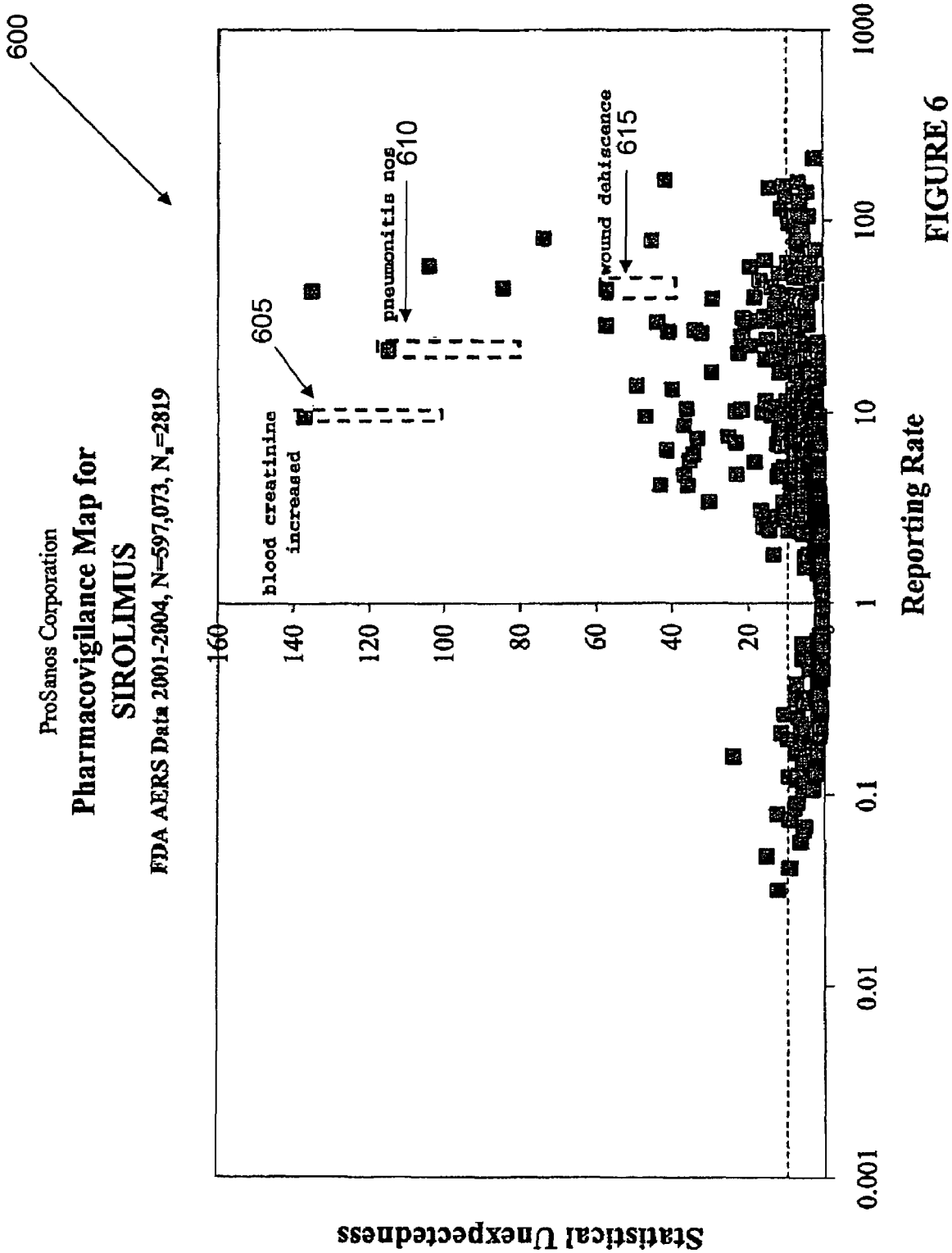
FIG. 6 is a display of a pharmacovigilance map for the drug SIROLIMUS which includes boxes that describe confidence limits for the proportional reporting rate and statistical unexpectedness of three selected adverse events, "blood creatinine increased", "pneumonitis nos [not otherwise specified]" and "wound dehiscence".

In the embodiments considered above, conditions are plotted as points on a graph. In a further embodiment, these points may be surrounded by boxes, ovals, or similar shapes to indicate the degree of statistical certainty, i.e. the confidence limits, related to the position of the point. These will be referred to as "confidence boxes", though they may have an oval or similar shape. FIG. 6 shows a graph 600 with "confidence boxes" around manually-designated points, chosen for this example to be "blood creatinine increased" 605, "pneumonitis [not otherwise specified]" 610, and "wound dehiscence" 615. Any adverse events of interest may be selected by the user and plotted with confidence boxes. A user would generally choose a set of adverse events of interest so as to avoid a confusing overlap of boxes on a particular plot. A user would make multiple plots if necessary to examine the confidence boxes for a large number of adverse events, while avoiding a confusing overlap of boxes. The boxes are calculated using a "bootstrap" approach. This involves taking a number of samples from the dataset and recalculating Reporting Rate and SU values on the data within the sample. In a typical embodiment, 20 random samples are generated, each containing 80% of the records in the data set. The variability among such samples can be characterized by a measure such as a standard deviation, or by a nonparametric measure such as the median absolute deviation. The variability in Reporting Rate (or relative risk) and in SU is then used to determine the confidence intervals which are represented in the height and width of the confidence box.

In the above embodiment, random samples are generated, each containing 80% of the records in the database. In a further embodiment, the samples are chosen so that each sample eliminates a randomly-chosen 20% of the drugs in the database. In other words, samples are chosen on a drug-by-drug basis, rather than on a record-by-record basis. Confidence boxes are generated as described above. The particular utility of this embodiment is for the detection of masking, also called cloaking, in spontaneous-reporting systems. The phenomenon of masking occurs when an extremely strong association between a drug and an adverse event suppresses the signals of disproportionality for other drugs with that adverse event. If 20 samples are generated with 20% elimination as described above, there is approximately a 99% likelihood that any given drug will be eliminated in at least one of the samples. If masking is occurring, elimination of an unduly influential drug will cause a large shift in the Reporting Rate and SU for several other drugs. This will produce a wide confidence boxes, warning of the potential for masking.

Confidence boxes are also useful in comparing graphs representing two or more drugs or vaccines, or other sets of conditions. Boxes which do not overlap indicate significant differences in the safety profile for the drugs under study.

Confidence boxes can be created for maps such as the map 500 shown in FIG. 5, in which the points on the map refer to individual drugs rather than to adverse-event codes.

Note that confidence boxes can also aid in the design of future clinical trials, or in planning for the integration of additional data sources, since a large box indicates a particular issue where further safety data is needed.

Additional Embodiments: Colored Points

Plotted points may be colored in a variety of ways to indicate stratification of the data reflected in each point. For example, points could be colored to reflect the male/female ratio corresponding to the given drug-adverse event combination. Colors can be scaled in a variety of visually-meaningful ways. Arbitrary color codes can be used, for example: green=male, red=female. Colors can represent a "temperature" scale, so that higher values correspond to "hotter" colors. Rather than coding a variable directly into a color scale, it is possible to use the color to represent a Z-score or other statistical significance score using a color. Appropriate color scales are discussed by Montag and others [Montag, 1999].

Figure 7:
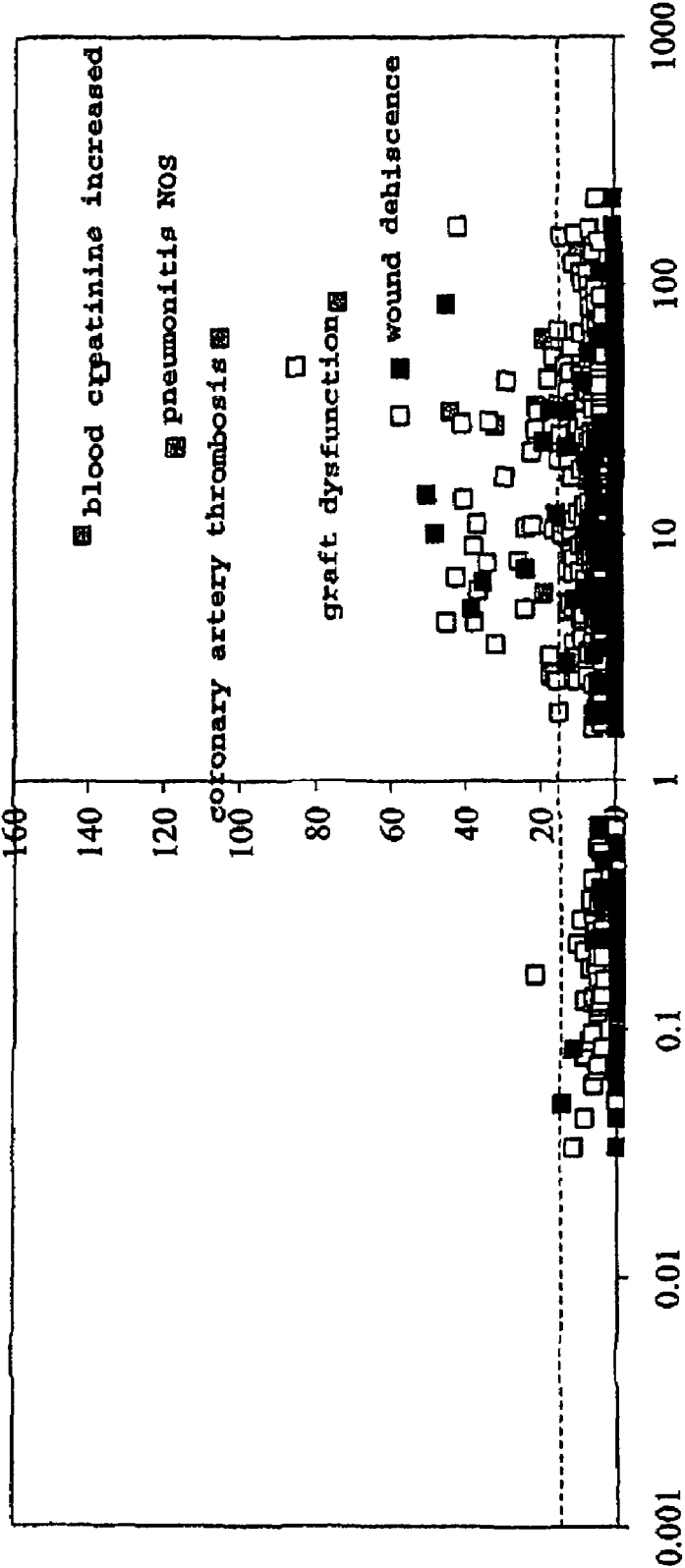
FIG. 7 is a display that an illustrates an example of the use of color in a pharmacovigilance map.

FIG. 7 shows a pharmacovigilance map 700 where the color of each dot has been chosen to indicate the relative death rate for each corresponding adverse event. The death rate is determined from outcome data contained in the AERS database. It should be noted because the instant drawings are not reproduced in color, the colors "black", "gray" and "white" have been used here. One skilled in the art would recognize that various different colors (in fact, any set of recognizable colors) could be used instead of the shades of grey disclosed in FIG. 7. In FIG. 7, the black dots indicate adverse events where death rate is significantly higher for SIROLIMUS patients than for those on other drugs. Gray dots indicate adverse events where the death rate is lower for SIROLIMUS than for other drugs. The black dot for "wound dehiscence", for example, is instructive. It indicates that wound dehiscence with SIROLIMUS has a more serious outcome than for other drugs. Such an observation may be important in setting priorities for safety investigations.

Many other uses of color are possible. Points can be colored to indicate gender ratios, age ranges, underlying diseases, or many other factors of use in safety investigations. Color could be used to compare safety results from two different populations or geographic areas. It could also be used to highlight differences in safety profiles between two related drugs, or between two different studies of a single drug. This could include comparison of pre-market vs. post-market safety data for a given drug or vaccine.

Additional Embodiments: Vectors

Figure 8:
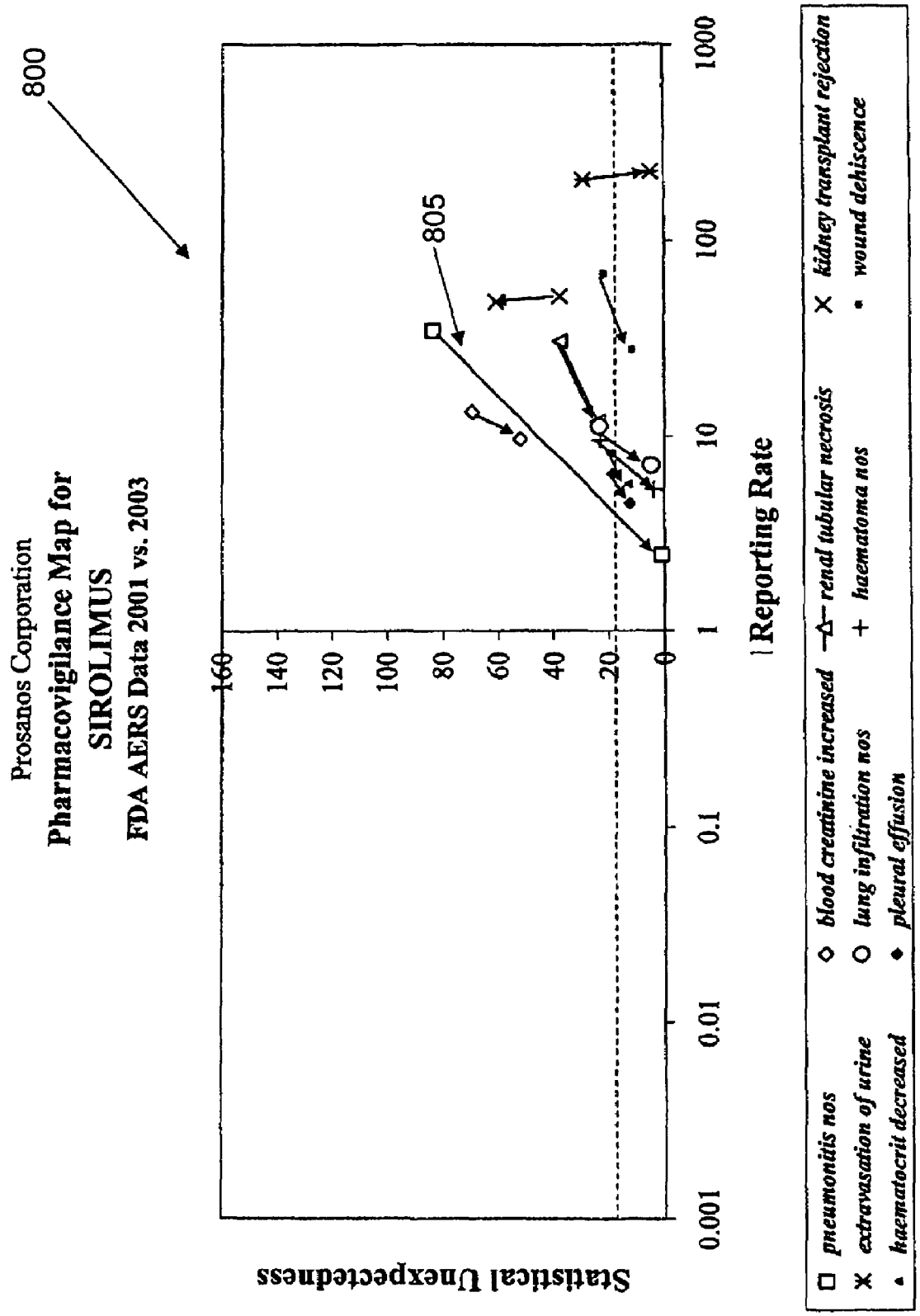
FIG. 8 is display that shows a pharmacovigilance map containing vectors useful for the comparison of two datasets regarding a particular drug, or two related drugs.

In the embodiments considered thus far, points are plotted to represent the Reporting Rate (or relative risk or odds ratio) and statistical unexpectedness corresponding to various conditions. In another embodiment, vectors are drawn from one point to another, where the first point represents a condition in one stratum or data set, and the second point represents the same condition in a second stratum or data set. In this manner, the data sets can be compared, since longer vectors will correspond to greater discrepancies between the data sets, and shorter vectors will correspond to high similarity between the data sets. The data sets could be two clinical trials of the same or related drugs, or could include spontaneous-reporting data or medical record data. FIG. 8 shows a pharmacovigilance map 800 for the drug SIROLIMUS during two different years, 2001 and 2003. Arrows are drawn from the RR and SU values for the earlier year (2001) to the corresponding values for the later year(2003). The longer the line, the greater the discrepancy between the two years. Notice in particular the long line 805 moving down and to the left for "pneumonitis nos". This indicates that this particular adverse event occurred significantly more often in 2001 than in 2003, and may indicate an important statistical difference between medical practice in the two years. In this example, it is likely that a reduction in the use of the use of SIROLIMUS in lung transplantation was responsible for the change [Groetzner, 2004].

Additional Embodiments: Trajectories

Certain embodiments of the present invention provide for constructing and plotting trajectories for specified Conditions of Interest as partitioning parameters like those described previously herein are varied systematically. As a specific example, using the moving-window partitioning described above would provide the basis for time-dependent characterizations that could reveal changes in adverse event/drug associations with time as drugs are used for longer periods of time, as other drugs are approved or recalled, for example. Such plots could consist of a graph with two lines, one representing statistical unexpectedness, and the other representing an association measure, both plotted as a function of time. Alternatively, the plots could consist of a line representing a trajectory in an X-Y space of statistical unexpectedness vs. association measure, with time as a parameter.

The size of the moving window can be adjusted to optimize the sensitivity and specificity of the pharmacovigilance data. Larger window sizes lead to greater sensitivity, that is, higher likelihood of observing statistically significant effects, because greater number of events will be included within the window. Smaller windows lead to better specificity, that is, fewer spurious observations because they reduce the likelihood that happenstance temporal trends in the data will lead to false positive associations.

The points plotted in trajectories may reflect data points within a moving window or neighborhood as discussed above, or they may reflect a cumulative collection of data points. For example, the points of a trajectory might reflect each quarter within the years 2001-2004, or they might reflect cumulative data by quarter from the first quarter of 2001 to the last quarter of 2004.

Trajectories can be used to track emerging safety issues, by plotting the evolution of SU and log(RR) for a particular drug-event combination over time. This may be helpful in post-market surveillance, where the relative risk for a particular drug-event combination could be monitored using data from an electronic medical record system or other surveillance system.

Figure 9:
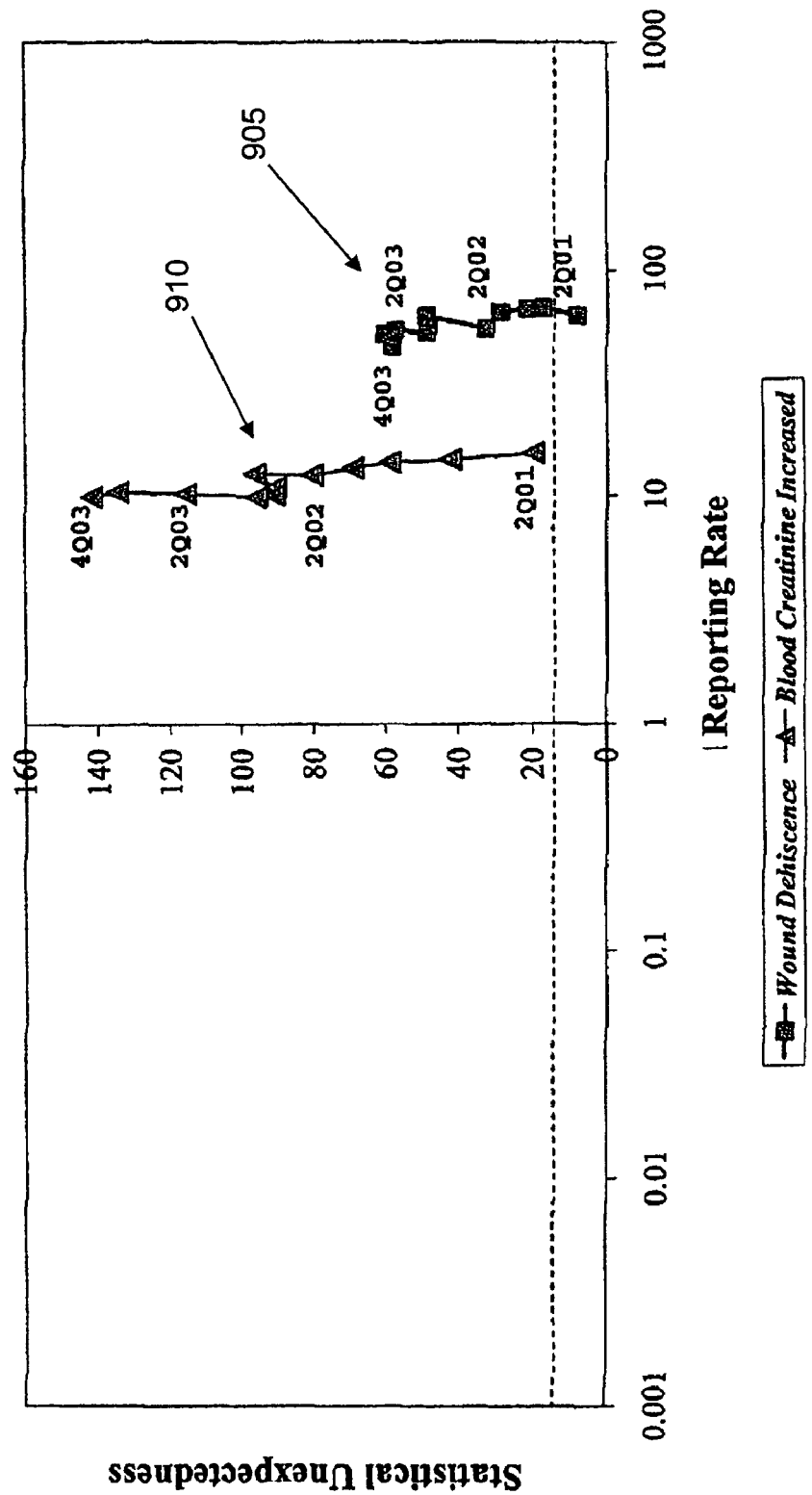
FIG. 9 is a display that shows a pharmacovigilance map which indicates the trajectory of two particular adverse effects over time, namely "wound dehiscence" and "blood creatinine increased".

FIG. 9 shows a display 900 of the trajectory over time of relative risk for SIROLIMUS with respect to two drug-adverse event combinations, "wound dehiscence" 905 and "blood creatinine increased" 910. Note that several different drug-event combinations could be plotted on a single graph, using different-colored lines or different patterns if desired, so as to increase the amount of information contained in a single graph, as long as a confusing overlap of lines is avoided. Multiple plots could be generated to avoid such a confusing overlap of lines. Time in quarters is designated by the labels on the graph. For both adverse events plotted, the proportional reporting rate remains relatively consistent and the statistical unexpectedness increases over time, as more cases are reported. This is the typical signature of a legitimate emerging safety issue, rather than a transient statistical anomaly.

In certain particular studies such as clinical trials, the independent variable in the moving window could represent the dose of a drug under study, rather than time. If an adverse event were dose-related, the corresponding trajectory would be seen to move in the direction of stronger association and greater statistical unexpectedness.

Further Embodiments

In certain embodiments, the present invention provides for incorporating medical and/or biological likelihood-of-association information included in pharmacovigilance databases. In some cases, it is possible to characterize the likelihood of a causal association between a drug and an adverse event for a particular patient. Strategies for this include "de-challenge," where it is observed whether or not the adverse event is alleviated by discontinuing the drug, and "re-challenge," where, when it is safe to do so, the suspect drug is re-administered to see if the adverse event worsens or re-occurs. In these cases, drug-adverse event associations may be semi-quantitatively labeled as "possible," "probable," "likely," etc. In this invention, we would consider these labels to be numerical markings ("0," "1," "2," "3," etc.) on the balls in the urn models. The mathematics herein would then apply to the sums of the markings on the balls, rather than to the count of balls chosen, but would otherwise remain the same.

A related notion could be used to incorporate information about particular genes or biochemical pathways affected by certain drugs, and about those genes and pathways that are involved in certain adverse events. To accommodate this, the balls in the urn would be marked with numerical vectors, with each element of the vector corresponding to a particular gene or biochemical pathway. For balls corresponding to drugs, the components of the vector would represent the strength of influence of that drug on the particular gene expression or biochemical pathway. For balls corresponding to adverse events, the components of the vector would represent the influence of the particular gene expression or biochemical pathway on the occurrence of the adverse event.

Certain additional embodiments provide for the development of pharmacovigilance analyses based on a sequence of related analyses of the type described in the preceding paragraphs. For example, once a potential drug/reaction association is identified from an analysis similar to that illustrated in FIGS. 1 and 2, this drug/reaction combination could be defined as a new Reference Condition, and the general procedure outlined here could be applied to analyze associations between this drug/reaction combination and all other drugs that appear in records listing this combination. Strongly associated drug/event and drug combinations would then point to potential adverse effects due to drug/drug interactions. Further insight into this possibility could be obtained by taking this drug/drug combination as Reference Condition A and analyzing its association with all adverse events that appear in records listing these two drugs.

Exemplary Computer System Implementation

Figure 3:
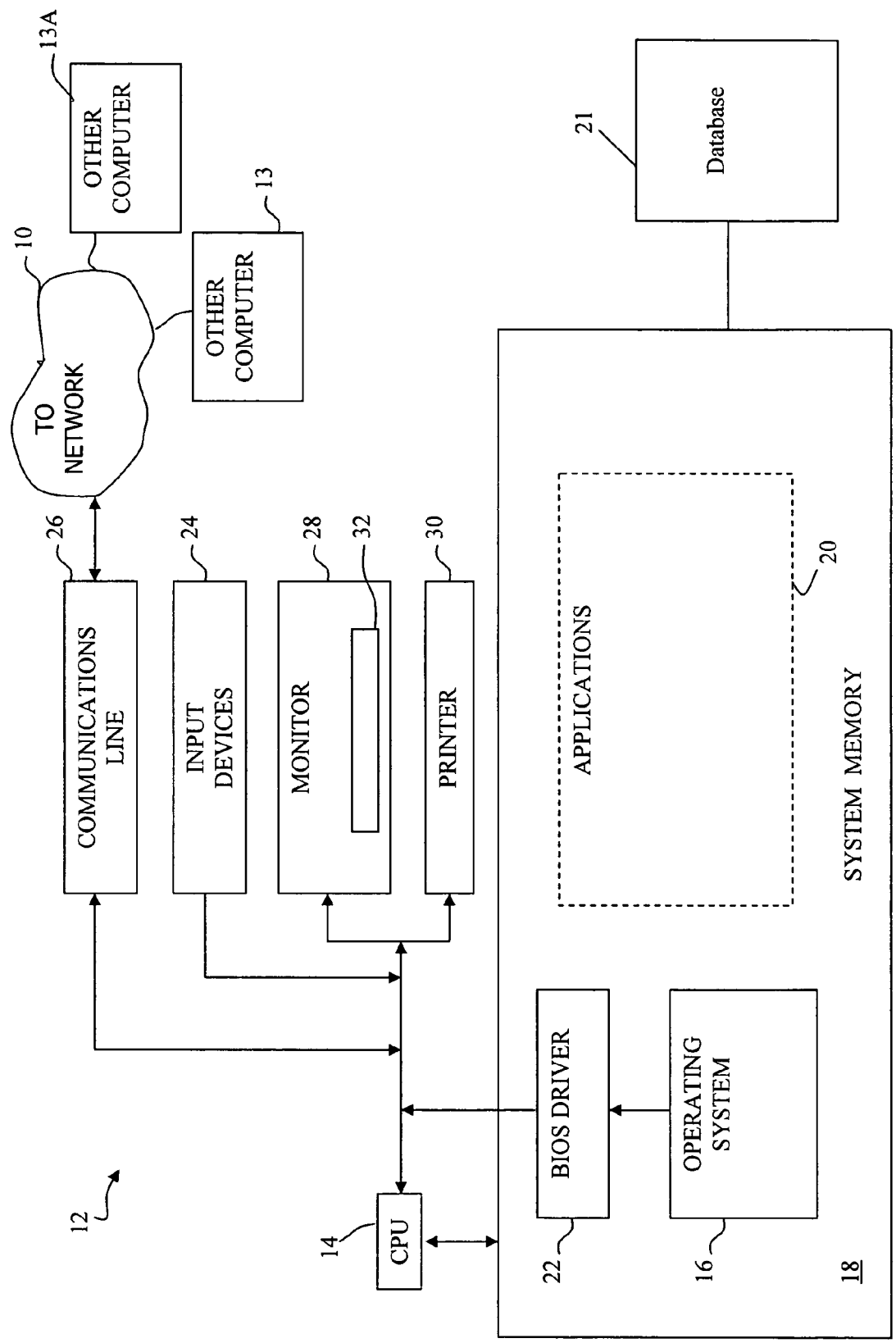
FIG. 3 is a diagram that illustrates a generic computing system that may be used to implement the present invention.

FIG. 3 illustrates the components of a generic computing system connected to a general purpose electronic network 10, such as a computer network. The computer network can be a virtual private network or a public network, such as the Internet. As shown in FIG. 3, the computer system 12 includes a central processing unit (CPU) 14 connected to a system memory 18. The system memory 18 typically contains an operating system 16, a BIOS driver 22, and application programs 20. In addition, the computer system 12 contains input devices 24 such as a mouse or a keyboard 32, and output devices such as a printer 30 and a display monitor 28, and a permanent data store, such as a database 21. The computer system generally includes a communications interface 26, such as an ethernet card, to communicate to the electronic network 10. Other computer systems 13 and 13A also connect to the electronic network 10 which can be implemented as a Wide Area Network (WAN) or as an internetwork, such as the Internet. Data is stored either in many local repositories and synchronized with a central warehouse optimized for queries and for reporting, or is stored centrally in a dual use database.

One skilled in the art would recognize that the foregoing describes a typical computer system connected to an electronic network. It should be appreciated that many other similar configurations are within the abilities of one skilled in the art and it is contemplated that all of these configurations could be used with the methods and systems of the present invention. Furthermore, it should be appreciated that it is within the abilities of one skilled in the art to program and configure a networked computer system to implement the method steps of the present invention, discussed earlier herein. For example, such a computing system could be used to implement the method of analyzing and displaying pharmacovigilance data as discussed earlier herein.

The present invention also contemplates providing computer readable data storage means with program code recorded thereon (i.e., software) for implementing the method steps described earlier herein. Programming the method steps discussed herein using custom and packaged software is within the abilities of those skilled in the art in view of the teachings herein.

Other embodiments of the invention will be apparent to those skilled in the art from a consideration of the specification and the practice of the invention disclosed herein. It is intended that the specification be considered as exemplary only, with such other embodiments also being considered as a part of the invention in light of the specification and the features of the invention disclosed herein. Furthermore, it should be recognized that the present invention includes the methods disclosed herein together with the software and systems used to implement the methods disclosed here.

List of Publications

The present application refers to the following publications. The referenced portions of each of these publications are incorporated herein in their entireties.

Agresti A, *Categorical Data Analysis* $2^{nd}$ Ed. J. W Wiley & Sons: New York, 2002.

Bate A et al. A Bayesian neural network method for adverse drug reaction signal generation. Eur J Clin Pharm 54:315-321, 1998.

Brown E G, Wood L, and Wood S. The medical dictionary for regulatory activities (MedDRA). Drug Safety 20(2):109-17, 1999.

DuMouchel W, Bayesian Data Mining in Large Frequency Tables with an Application to FDA Spontaneous Reporting System, American Statistician, 53:197-190, 1999.

Du Mouchel W and Pregibon D. Empirical Bayes screening for multi-item associations. Seventh ACM SigKDD International Conference on Knowledge Discovery and Data Mining. 2001.

Evans, S J W, Waller P C, and Davis S. Use of proportional reporting ratios (PRRs) for signal generation from spontaneous adverse drug reaction reports. Pharmacoepidemiology and Drug Safety 10:483-486, 2000.

Gordon A D, Classification ($2^{nd}$. ed.), Chapman and Hall: Norwell, Mass., 1999.

Gould A L, Practical Pharmacovigilance Analysis Strategies, Pharmacoepidemiology and Drug Safety. 12:423-458, 2003.

Groetzner, J et al. Airway anastomosis complications in de novo lung transplantation with sirolimus-based immunosuppression. J Heart Lung Transplant. 23(5):632-8, 2004.

Heeley E, Wilton L V, and Shakir S A W, Automated Signal Generation in Prescription-Event Monitoring, Drug Safety 25:423-432, 2002.

Johnson N L, Kotz S, and Kemp A W, Univariate Discrete Distributions ($2^{nd}$. ed.), J. W. Wiley & Sons: New York, 237-253, 1992.

Mielke P W Jr. and Berry K J, Permutation Methods: A Distance Function Approach. Springer Verlag: New York, 273, 2001.

Montage ED. The Use of Color in Multidimensional Graphical Information Display. IS&T/SID Seventh Color Imaging Conference, Scottsdale, Ariz., 1999.Downloaded from the Internet on Jul. 25, 2005 from [http://www.cis.rit.edu/people/faculty /montag/PDFs/paper43. pdf] the Center for Imaging Science RIT website with the extension "/people/faculty/Montag/PDFs/paper43.pdf".

Schield M, Simpson's Paradox and Cornfield's Conditions, AMERICAN STATISTICAL ASSOCIATION PROCEEDINGS OF THE SECTION ON STATISTICAL EDUCATION, 106-111, 1999.

Szarfman A, Machado S G, and O'Neill R T. Use of screening algorithms and computer systems to efficiently signal higher-than-expected combinations of drugs and events in the US FDA's spontaneous reports database. Drug Safety 25(6): 381-392, 2002.

U.S. Department of Health and Human Services, Food and Drug Administration, "Guidance for Industry: Food Pharmacovigilance Practices and Pharmacoepidemiologic Assessment". Download from the Internet at [http://www.fda.gov/cber/gdlns/pharmacovig.pdf] the FDA government website with the extension "/cber/gdlns/pharmacovig.pdf", 20 Jul. 2005.

Westfall P, and Young S, Resampling based Multiple Testing, J. W Wiley & Sons: New York, 1993.

Wolfinger R, et al., Assessing Gene Significance from cDNA Microexpression Data via Fixed Model, J. Computational Biology 8:625-637, 2001.

What is claimed is:

1. A computer-implemented method of analyzing a dataset of pharmacovigilance data, comprising:
    (a) determining a sample size-independent measure of association between two conditions of interest in the dataset of pharmacovigilance data on a suitably programmed computing device;
    (b) analyzing a hypergeometric distribution to determine a measure of statistical unexpectedness between the conditions of interest in said dataset on a suitably programmed computing device, wherein said distribution is based on an urn model under a hypothesis that said conditions are statistically independent; and
    (c) displaying the measure of association with the measure of the statistical unexpectedness to identify, a significant association between the conditions of interest on a suitably programmed computing device.

2. The computer-implemented method according to claim 1, wherein the dataset comprises binary data and the measure of association comprises a reporting ratio $RR_{AB}$ defined as $$RR_{AB} = \frac{N_{AB}N}{N_A N_B},$$

where a total number of records in the dataset is N, a total number of records satisfying a first of the two conditions of interest is $N_A$, a total number of records satisfying a second of the two conditions of interest is $N_B$, and a total number of records satisfying both the first and second conditions of interest is $N_{AB}$.

3. The computer-implemented method according to claim 2, wherein the significant association between the two conditions of interest is determined if the following criteria are satisfied $$RR_{AB} < 1 \text{ and } C_{AB} = P\{N_{AB} \leq n\} < \theta$$

$$RR_{AB} > 1 \text{ and } C'_{AB} = P\{N_{AB} \geq n\} < \theta$$

where $\theta$ represents a small significance threshold probability for significance, $C_{AB}$ represents the cumulative probability ($C_{AB} = P\{N_{AB} \leq n\}$), and $C'_{AB}$ represents the complimentary probability $C'_{AB} = P\{N_{AB} \geq n\}$,
    wherein statistical unexpectedness ($U_{AB}$) of an observed response $N_{AB}$ is the reciprocal of the corresponding cumulative or complementary probability and defined as following $$U_{AB} = 1/C_{AB} \text{ if } RR_{AB} < 1 \text{ and } U_{AB} = 1/C'_{AB} \text{ if } RR_{AB} > 1.$$

4. The computer-implemented method according to claim 2, wherein the first condition of interest is a fixed reference condition, and the second condition of interest is range of relevant comparison conditions.

5. The computer-implemented method according to claim 4, wherein the first condition of interest is a presence of a drug and the second condition of interest is an adverse event.

6. The computer-implemented method according to claim 3, wherein the significance threshold is adjusted for multiple comparisons.

7. The computer-implemented method according to claim 6, wherein the significance threshold is adjusted using the Bonferroni approximation wherein the significance threshold is adjusted to θ/M where M represents the number of comparisons between the first and second conditions of interest.

8. The computer-implemented method according to claim 3, wherein displaying the measure of association comprises separately indicating negative associations with reporting ratios less than one from positive associations with reporting ratios greater than one.

9. The computer-implemented method according to claim 3, wherein displaying the measure of association comprises displaying statistically significant absent conditions in which $N_{AB}=0$.

10. The computer-implemented method according to claim 1, further comprising partitioning the dataset into subsets and performing steps (a)-(c) for each subset of the dataset.

11. The computer-implemented method according to claim 10, wherein the step of partitioning the dataset into subsets comprises partitioning into fixed size moving window partitions based on an index of records in the dataset or on one or more fields in the records in the dataset.

12. The computer-implemented method according to claim 11, wherein the fields in the records comprise one of a reporting date, a gender, or an age.

13. The computer-implemented method according to claim 11, wherein the step of partitioning the dataset into subsets comprises using a nearest neighbor partitioning which applies a distance function to the one of more fields in the records in the dataset.

14. The computer-implemented method according to claim 11, wherein the step of partitioning the dataset comprises using cluster based partitioning.

15. The computer-implemented method according to claim 4, further comprising combining the first and second conditions of interest, when a significant association between the first and second conditions of interest is determined, as a new fixed first condition of interest and repeating steps (a)-(c) with a new second condition of interest.

16. The computer-implemented method according to claim 15, wherein the new first condition of interest is a combination of a drug and an adverse event while the new second condition of interest is another drug.

17. The computer-implemented method according to claim 10, further comprising constructing and plotting conditions of interest while the partitioning step varies partitions based on selecting different fields and/or values of fields used for partitioning the dataset into subsets.

18. The computer-implemented method according to claim 3 wherein the step of determining significant associations comprises using likelihood-of-association information from other medical and biological databases.

19. The computer implemented method according to claim 18, wherein the biological databases comprise information from biological pathways affected by each drug, encoded in the form of a numerical vector.

20. The computer implemented method according to claim 1, wherein the measure of association is a relative risk or an odds ratio.

21. The computer implemented method according to claim 4, wherein pairs of a first condition and a second condition include one among a particular drug and a second drug taken with the particular drug, or a first adverse event and a second adverse event that occurs with the first adverse event.

22. The computer implemented method according to claim 2, further comprising:
 (a) taking a number of samples from the dataset;
 (b) recalculating the reporting ratio and the measure of unexpectedness for each of the number of samples; and
 (c) displaying a confidence box around an adverse event based on corresponding points for that adverse event for each of the calculated and recalculated reporting ratios and the measure of unexpectedness for each of the number of samples.

23. The computer implemented method according to claim 22, wherein each of the samples contain between 40-80% of the records in the database.

24. The computer implemented method according to claim 22, wherein each of the samples are selected to eliminate records containing a certain percentage of drugs in the dataset.

25. The computer implemented method according to claim 1, wherein the measure of association is displayed using color coded values indicative of either the data underlying the particular association or a significance of the association.

26. The computer implemented method according to claim 10, wherein corresponding measures of association displayed as points from the corresponding subsets of data are visually linked together using vectors.

27. The computer implemented method according to claim 1, further comprising:
 (a) taking a number of samples from the dataset;
 (b) recalculating and displaying as points the reporting ratio and the measure of unexpectedness for each of the number of samples; and
 (c) displaying points corresponding to the same pair of conditions across the number of samples in an integrated display by a vector.

28. The computer implemented method according to claim 10, wherein the measure of association and the statistical unexpectedness for each subset is plotted on a graph as a trajectory in which the variations across the subsets are indicative of variations in time or dosage.

29. The computer implemented method according to claim 28, wherein the subsets indicate data collected over time, and wherein if the measure of association remains relative constant while the measure of statistical unexpectedness increases over time, a safety issue is determined.

30. A system that includes a central processing unit (CPU) for analyzing a dataset of pharmacovigilance data, comprising:
 (a) an input unit for accessing the dataset of pharmacovigilance data;
 (b) a processing unit configured to:
  (i) determining a sample size-independent measure of association between two conditions of interest in the dataset of pharmacovigilance data; and
  (ii) analyzing a hypergeometric distribution to determine a measure of statistical unexpectedness between the conditions of interest in said dataset, wherein said distribution is based on an urn model under a hypothesis that said conditions are statistically independent; and
 (c) a display unit for displaying the measure of association with the measure of the statistical unexpectedness to identify a significant association between the conditions of interest.

31. A computer program product on a computer readable storage medium that, when executed on a computing system, analyzes a dataset of pharmacovigilance data, the program product comprising:

(a) code for determining a sample size-independent measure of association between two conditions of interest in the dataset of pharmacovigilance data;

(b) code for analyzing a hypergeometric distribution to determine a measure of statistical unexpectedness between the conditions of interest in said dataset, wherein said distribution is based on an urn model under a hypothesis that said conditions are statistically independent; and (c) code for displaying the measure of association with the measure of the statistical unexpectedness to identify a significant association between the conditions of interest.

* * * * *

UNITED STATES PATENT AND TRADEMARK OFFICE
CERTIFICATE OF CORRECTION

PATENT NO.        : 7,650,262 B2                              Page 1 of 1
APPLICATION NO.   : 11/257395
DATED             : January 19, 2010
INVENTOR(S)       : Pearson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1121 days.

Signed and Sealed this

Ninth Day of November, 2010

David J. Kappos
*Director of the United States Patent and Trademark Office*